United States Patent
Archer

(10) Patent No.: US 9,833,531 B1
(45) Date of Patent: Dec. 5, 2017

(54) AROMATHERAPY RING FOR SHOWER HEAD

(71) Applicant: Sheri Ann Archer, Englewood, CO (US)

(72) Inventor: Sheri Ann Archer, Englewood, CO (US)

( * ) Notice: Subject to any disclaimer, the term of this patent is extended or adjusted under 35 U.S.C. 154(b) by 0 days.

(21) Appl. No.: 15/249,368

(22) Filed: Aug. 27, 2016

(51) Int. Cl.
    *A61L 9/04*     (2006.01)
    *A61L 9/03*     (2006.01)
    *B05B 1/18*     (2006.01)

(52) U.S. Cl.
    CPC   *A61L 9/03* (2013.01); *A61L 9/04* (2013.01); *B05B 1/18* (2013.01); *A61L 2209/15* (2013.01); *Y10S 239/11* (2013.01)

(58) Field of Classification Search
    CPC .......... A61L 9/03; A61L 2209/15; A61L 9/04; B05B 1/18; Y10S 239/11
    USPC .......... 239/34, 289, 525, 530, 575, DIG. 11; 422/123
    See application file for complete search history.

(56) References Cited

U.S. PATENT DOCUMENTS 7,975,936 B2 * 7/2011 Paoluccio ............. B05B 7/0425
    239/525

* cited by examiner

*Primary Examiner* — Steven J Ganey
(74) *Attorney, Agent, or Firm* — Edwin H. Crabtree; Ramon L. Pizarro

(57) ABSTRACT

An aromatherapy ring made of soft, flexible silicon or like material. The ring includes a split ring body with an open trough therearound for receiving aroma liquid. The split ring body is adapted for wrapping around a shower filter or a shower head. The ring body includes first and second ends with magnets or like attaching means for engaging each other and holding the ring in a horizontal position on the shower filter or shower head. When warm or hot water passes through the shower filter or shower head, the aroma liquid is heated, thus providing a fragrance for aromatherapy, when taking a shower.

11 Claims, 2 Drawing Sheets

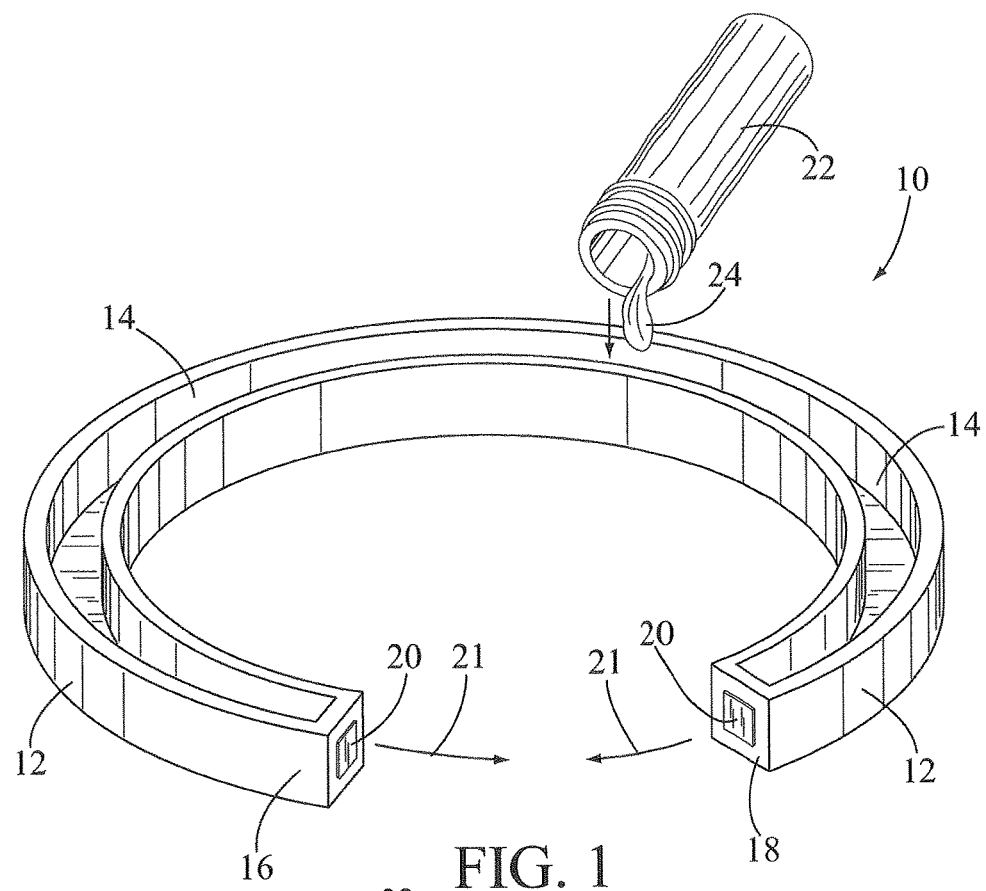
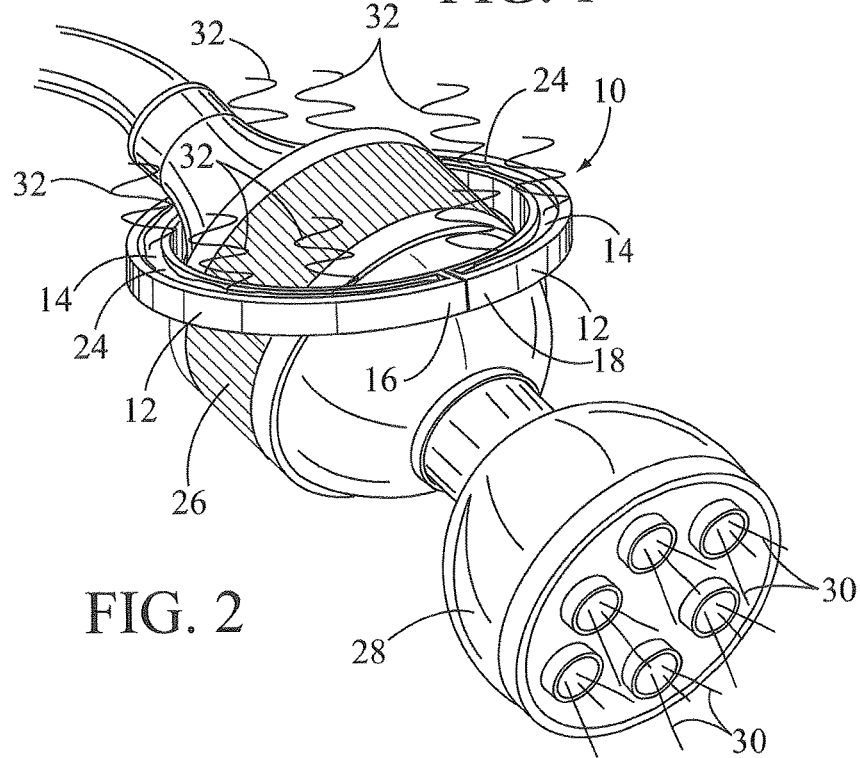

AROMATHERAPY RING FOR SHOWER HEAD

BACKGROUND OF THE INVENTION (a) Field of the Invention

This invention relates to a ring for holding aroma liquids and more particularly, but not by way of limitation, to a flexible, silicon, split ring adapted for wrapping around a shower filter or shower head and held thereon. The split ring includes a ring body having an open tray for holding an aroma liquid and providing a fragrance during a shower.

(b) Discussion of Prior Art

In U.S. Pat. No. 6,581,220 to Yekutiely et al., a method and apparatus for taking an aromatherapy shower is disclosed. The apparatus includes a conduit, a one-way valve, and a vacuum pump connected to a shower head and water supply. This complex shower pumping system is used to introducing an aroma liquid into a warm water stream. The subject invention eliminates the need for adding any plumping fixtures to the water supply of an existing shower.

SUMMARY OF THE INVENTION

In view of the foregoing, it is a primary objective of the subject invention to provide a simple, yet efficient, way of heating an aroma liquid during a shower and thus provide aromatherapy and fragrance, when taking a warm shower.

Another object of the invention is the ring includes a split ring body, which easily wraps around a portion of different types and sizes of shower filters or shower heads.

Still another object of the invention is the split ring body includes an open trough therearound, which can quickly be filled and refilled with aroma liquid.

The subject invention is an aromatherapy ring made of soft, flexible silicon or like material. The ring includes a split ring body with an open trough therearound for receiving aroma liquid. The split ring body is adapted for wrapping around a shower filter or a shower head. The ring body includes first and second ends with magnets or like attachment means for engaging each other and holding the ring in a horizontal position on the shower filter or shower head.

These and other objects of the present invention will become apparent to those familiar with shower filters and shower heads and the use of an aroma liquid when reviewing the following detailed description, showing novel construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments in the present invention according to the best modes presently devised for the practical application of the principles thereof, and in which:

FIG. 1 is a perspective view of the subject aromatherapy ring with a split ring body and open trough. A container is shown pouring aroma liquid into the open trough.

FIG. 2 is a perspective view of the ring received around a portion of a shower filter.

DETAILED DESCRIPTION OF THE PREFERRED EMBODIMENTS

Figure 3:
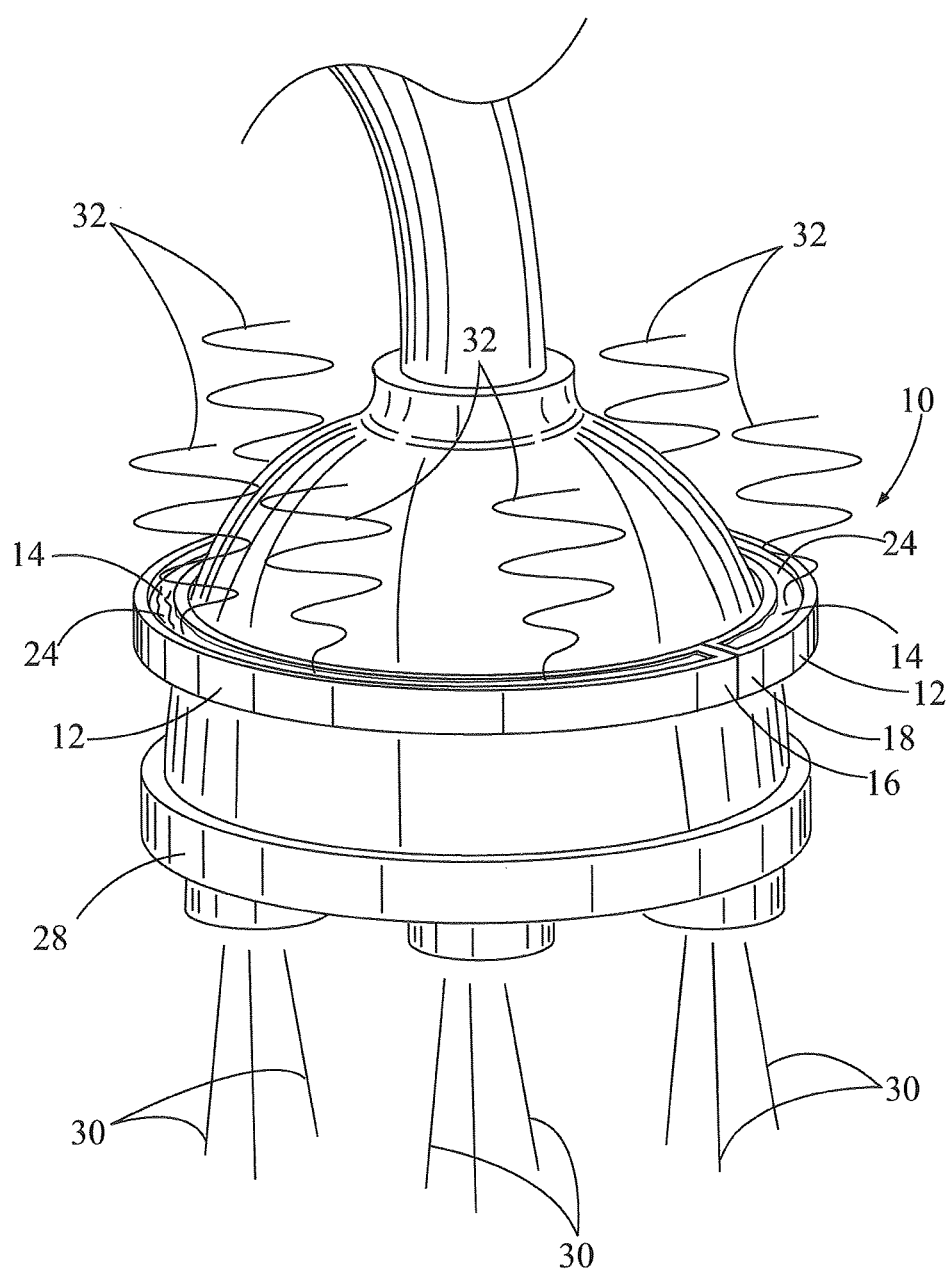
FIG. 3 is a perspective view of the ring received around a portion of a shower head.

In FIG. 1, a perspective view of the subject aromatherapy ring is shown having general reference numeral 10. The ring 10 includes a split ring body 12 with an open trough 14 therearound. The ring body 12 is made of a flexible, silicon or like material for ease in handling and cleaning. The body 12 is shown with a first end 16 and a second end 18. The ends 16 and 18 include magnets 20, embedded in the ends to prevent moisture from rusting the magnets. The magnets 20 are used for securing the ends together and closing the ring body, as shown by arrows 21. While the magnets are shown, it can be appreciated that various types of fasteners, not subject to be corroded by moisture could be used equally well with the ring 10.

In this drawing, a container 22 is shown holding an aroma liquid 24 and pouring the liquid into the open trough 14.

In FIG. 2, a perspective view of a shower filter 26 is shown attached to a shower head 28. In this drawing, the ring body 12 is shown received around a portion of a shower filter 26 and held thereon using the magnets 20 for securing the ends 16 and 18 together. It should be noted, the ring 10 is held in a horizontal position on the shower filter 26 so that the aroma liquid 24 does not spill out the open trough 14.

When warm water 30 or hot water passes through the shower filter 26 and out the shower head 28, the water heats the aroma liquid 24 in the trough 14. At this time, a fragrance 32 moves upwardly form the open trough for providing an aromatherapy shower.

In FIG. 3, another perspective view of the ring 10 is shown. In this drawing, the split ring body 12 is received around a portion of a shower head 28. Also shown in this drawing is the fragrance 32 moving upwardly from the heated aroma liquid 24 in the open trough 14.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

The embodiments of the invention for which as exclusive privilege and property right is claimed are defined as follows:

1. An aromatherapy ring adapted for mounting around a portion of a shower filter or shower head, the ring comprising:
    a split ring body with an open trough therearound, the open trough adapted for receiving aroma liquid therein, the split ring body including a first end and a second end, the split ring body made of a flexible silicon or like material; and
    a first magnet mounted in the first end of the split ring body and a second magnet mounted in the second end of the split ring body, the first and second magnets for securing the split ring body on the shower filter or shower head.

2. The ring as describe in claim 1 wherein the first and the second magnets are embedded inside the first and second ends of the split ring body.

3. The ring as described in claim 1 wherein the first magnet in the first end of the split ring body and the second magnet in the second end of the split ring body hold the ring body in a horizontal position on the shower filter or shower head.

4. An aromatherapy ring adapted for mounting around a portion of a shower filter or shower head, the ring comprising:
- a split ring body with an open trough therearound, the open trough adapted for receiving aroma liquid therein, the split ring body including a first end and a second end; and
- means for attaching the first end of the split ring body to the second end of the split ring body, the means for attaching used to secure the split ring body on the shower filter or the shower head.

5. The ring as described in claim 4 wherein the means for attaching is a magnet mounted in the first end and a magnet mounted in the second end of the split ring body.

6. The ring as described in claim 5 wherein the magnets in the first end and the second end of the split ring body hold the ring body in a horizontal position on the shower filter or shower head.

7. The ring as described in claim 4 wherein the ring body is made of a flexible silicon or like material.

8. An aromatherapy ring adapted for mounting around a portion of a shower filter or shower head, the ring comprising:
- a split ring body with an open trough therearound, the open trough adapted for receiving aroma liquid therein, the split ring body including a first end and a second end; and
- means for attaching embedded inside the first end of the split ring body to the second end of the split ring body, the means for attaching used to secure the split ring body on the shower filter or the shower head.

9. The ring as described in claim 8 wherein the means for attaching is a first magnet embedded inside in the first end and a second magnet embedded inside of the second end of the split ring body.

10. The ring as described in claim 9 wherein the magnets in the first end and the second end of the split ring body hold the ring body in a horizontal position on the shower filter or shower head.

11. The ring as described in claim 8 wherein the ring body is made of a flexible silicon or like material.

* * * * *